Figure 1:
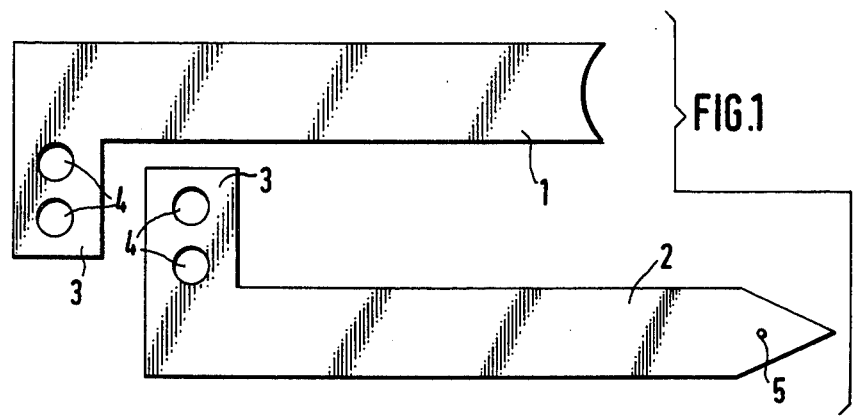

United States Patent [19]

Tauschinski

[11] 4,147,165

[45] Apr. 3, 1979

[54] SEPARABLE NEEDLE FOR INSERTING A CATHETER INTO THE BLOOD STREAM

[76] Inventor: Stefan O. Tauschinski, Gatterburggasse, 15, Wien, Austria, 1190

[21] Appl. No.: 785,452

[22] Filed: Apr. 7, 1977

[30] Foreign Application Priority Data

Apr. 15, 1976 [AT] Austria .................................. 2783/76
Dec. 21, 1976 [AT] Austria .................................. 9477/76

[51] Int. Cl.² .............................................. A61M 5/34
[52] U.S. Cl. ................................. 128/214.4; 128/221; 128/DIG. 16
[58] Field of Search ............ 128/214.4, 221, DIG. 16, 128/348, 347

[56] References Cited

U.S. PATENT DOCUMENTS

| 3,330,278 | 7/1967 | Santomieri | 128/221 X |
| 3,677,244 | 7/1972 | Hassinger | 128/214.4 |
| 4,037,599 | 7/1977 | Raulerson | 128/214.4 |
| 4,054,136 | 10/1977 | Zeppelin | 128/214.4 |

*Primary Examiner*—Dalton L. Truluck
*Attorney, Agent, or Firm*—John J. Dennemeyer

[57] ABSTRACT

A separable catheter needle for inserting a flexible vessel catheter into a blood vessel is adapted to be separated after taking a blood sample and comprises a needle tube of metallic material with a gripping and catheter inserting portion consisting of several elements made preferably of thermoplastic material. The needle tube consists of two tube halves which are assembled and bonded together along their meeting edge. An elastic or plastic sealing element is introduced into the assembled needle tube so that it engages its inner wall to provide a sealing of the tube against air and liquid. The rearward end of the needle tube has integral wing members which are covered by a gripping plate device consisting of a grooved central portion and of two lateral plate elements which fit over the tube and its wing members. The lateral plate elements cooperate with the wing elements to provide a mutual interconnection. The lateral plate elements have a rearward extension with a groove that increases axially from the grooved central portion of the gripping plate to provide a seat for receiving the conical rear end portion of the sealing element.

11 Claims, 8 Drawing Figures

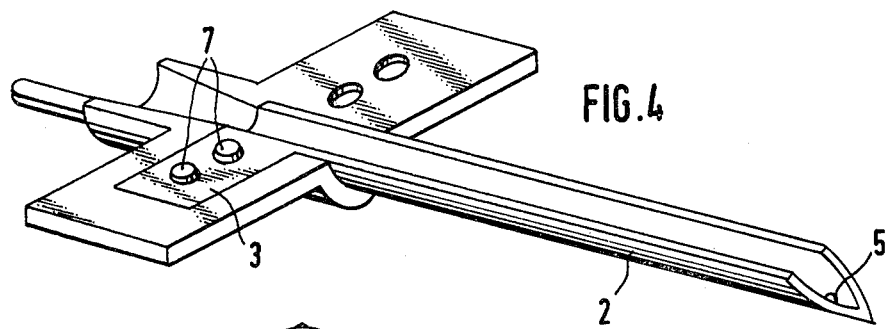
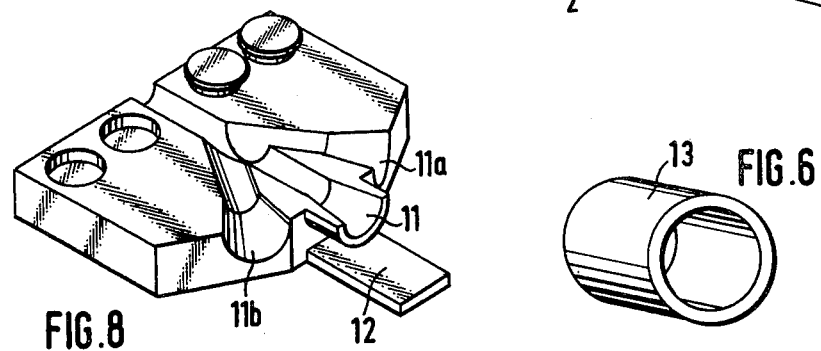
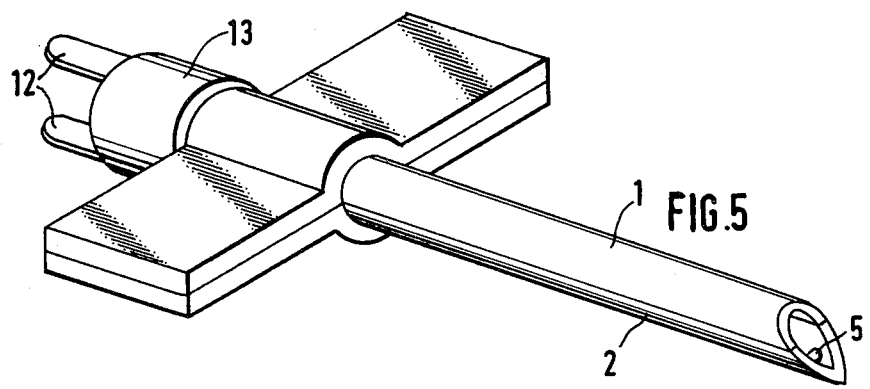
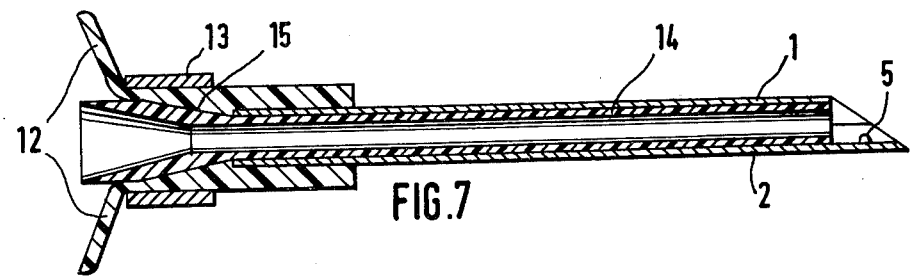

SEPARABLE NEEDLE FOR INSERTING A CATHETER INTO THE BLOOD STREAM

In the field of medicine and especially in hospitals the use of vessel catheters which are inserted into the blood stream of a patient obtain an ever increasing importance. The methods used hitherto for this purpose, such as the operational insertion (venae sectio), the insertion through a large diameter injection needle or a previously inserted metal spiral represented for the patient as well as for the practicing doctor many inherent dangers and complications so that much effort has been made to find safer and simpler methods. The vessel catheters in use today carry at their rearward extremity a rigid cone which facilitates a rapid and sterile change of the transfusion or infusion tube. On the other hand this cone prevents the withdrawal of an injection needle necessary for introducing the catheter. Attempts to secure this sharp needle outside the body at the end of the cathether have been unsatisfactory. For this reason various longitudinally separable needle arrangements have been proposed which, after completion of their insertion function, may be removed from the body and separated from the catheter by separating, breaking open or tearing.

The state of the art shows in the patent and professional literature a number of proposals whose aim is to provide a lateral separation of the used needle from the catheter. A disadvantage of such an injection needle is the sharp crescent-shaped rear edge of the needle grinding which can damage or even sever the catheter during withdrawal of the needle.

This danger described in the medical literature often as being the cause for catheter embolisms with resulting death relates to all known needles for which a longitudinal separation is provided. A number of proposals for designing separable needles for the introduction of vessel catheters use as base material punched blanks of sheet metal which are formed into a tube provided with a weakening line and ground subsequently to a slanted configuration. All these needles carry at their rearward end or just before it wings which extend laterally or upwardly, and intended to serve as grips to assist in their insertion and also as an opening element. All these different versions present an additional common disadvantage in that due to its manufacture from a sheet metal strip formed into a tube a gap is created at the meeting line of the edges and permits the access of air and liquid. The result is that when a clogged vein is punctured blood escapes from the gap and the injection point as well as the catheter on the inside are soiled. Since the introduction of a relatively long catheter requires a certain time this escape of blood can be considerable, and furthermore a bacterial infection of the catheter or the puncture area can occur.

A separable needle is already known in which a band holds together from the outside two mirror-image half cups of metal to form a tube which can contribute in providing a sealing of the needle to the outside. However, this assembling arrangement makes the needle diameter larger which adversely increases the difference between the insertion canal and the catheter diameter. Furthermore in this arrangement the outer jacket of the needle is to consist of a material which shrinks under heat or of a silicon rubber which has also a negative effect on the sliding property of the needle as it makes the insertion more difficult and causes the patient more pain.

The known open or separable needles which are considered to be suitable for the introduction of vessel catheters have the common disadvantage that they form a closed system together with the catheter. The catheter is already positioned in the needle or is pushed forward directly after the puncture. This procedure causes some serious disadvantages. A practicing doctor is often not able to determine when or if the needle with the catheter inside of it is actually in the blood vessel of the patient. This is particularly the case when the catheter is made of opaque material or its lumen part is closed by a madrel. In case the catheter is filled with air, even when the needle point is properly located in the blood vessel, the blood will enter only when the catheter is not tightly closed at its end so that the air can escape. In a transparent catheter which is air permeable at its end it is possible to recognize the inflow of blood when the injection needle is in a proper position, which is of special importance when deeper lying vessels are punctured, but this is not desirable because the blood tends to coagulate quickly in the narrow lumen of the catheter and can thus cause a clogging by thrombin formation. This type of situation limits the time available for inserting a relatively long catheter. In each simple intravenous or also intra-arterial injection the puncture is carried out with a needle which is mounted the injection needle, wherein by a light aspiration of blood from the punctured vessel the proper positioning of the needle point is checked. However, this simple control is not possible in this manner with any of the known separable injection needles because a direct coupling of the needle tube to an injection syringe is not provided. Even if this were possible the aspiration would not have the desired effect because the known separable needle tubes are not air tight so that only air or blood foam would be sucked into the syringe.

The properties of an injection needle tube for vessel catheters generally desired by the doctor and the hospital may be summarized as follows: the needle must have a sharp point so that it is able to penetrate easily even leathery skin and tough connective tissue without requiring much force. The needle point should have such a form that a catheter which has been pushed through may be withdrawn when necessary, without being thereby damaged or cut off, so that a correction of a wrong position of the catheter is possible. The needle tube should be so designed that it may be mounted on an injection syringe by means of which the puncturing of a vessel is then carried out. The needle should be sealed to such an extent that when its point is correctly positioned in the blood vessel blood may be sucked in by means of the syringe without also sucking in at the same time air from the outside. These improved properties of the needle relative to the present state of the art would substantially facilitate the introduction of a vessel catheter for the practicing doctor and make its handling no longer dangerous for the patient. The action could be compared almost with an intravenous or intra-arterial injection. After removal of the syringe the tube is to be coupled easily and rapidly with a device which makes possible a sterile and sensitive insertion of a correspondingly long vessel catheter. After the insertion and subsequent withdrawal of the needle tube from the body of the patient it is to be removed by separation without exerting much force from the catheter end. As it concerns an instrument that is used only one time it is also important to consider the cost of its manufacture.

It is an object of the present invention to fulfil all the requirements necessary in actual practice. In this respect ways and means have also been found to make the construction of the tubes sufficiently simple that an efficient mass production without much expenditure is now possible.

The object of the invention is to provide a needle tube which is designed for the introduction of a flexible vessel catheter into a blood vessel and after completing this function may be removed by a longitudinal separation from the catheter. It consists of a tubular element made of metal and of a grip-and catheter insertion portion which is preferably of a thermoplastic material, and characterized in that the needle tube is provided through its entire length with an elastic tubular sealing element which engages in sealing relationship the metallic and non-metallic parts of the assembled needle tube on the inside thereof. This needle tube consists of two parts made of a metallic material and has a semicircular section. The two parts are placed upon each other and bonded together along the longitudinal edges so as to form a round tube when assembled.

A separable catheter needle provided with features described in respect of this invention fulfils all requirements for allowing a simple, rapid, sterile and particularly danger-free application of vessel catheters. Furthermore the construction of the needle tubes is so designed that its manufacturing process whose individual phases are carried out automatically do not require much expenditure with respect to the material used and the mechanical equipment so that an efficient and inexpensive production can be assured.

Figure 2:
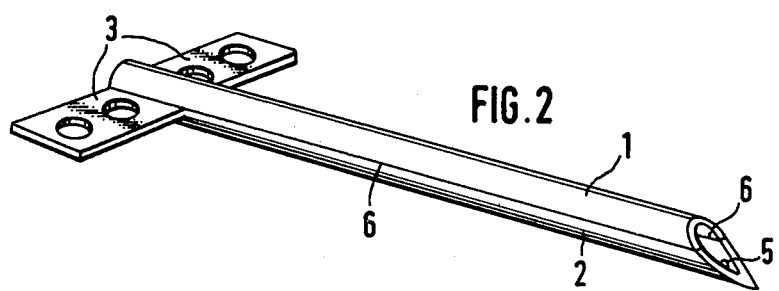
Figure 3:
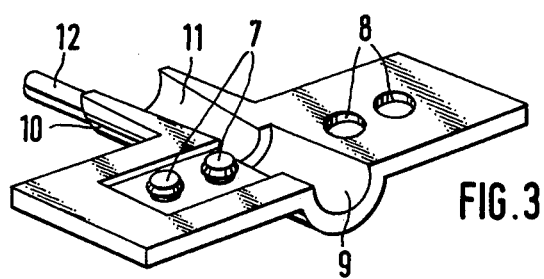

These and other objects and features of the invention will be recognized more clearly from the description of an embodiment of the invention illustrated in the accompanying drawings and in which, FIG. 1 shows two sheet metal blanks from which the needle tube is formed;

FIG. 2 is a perspective view of the upper and lower tube portions formed from the blanks shown in FIG. 1, FIG. 3 is a perspective view showing one of the two symmetrical portions of the gripping plate, FIG. 4 is a perspective view of the lower tube portion positioned inside the gripping plate portion of FIG. 3, FIG. 5 is a perspective view of an assembled needle tube, FIG. 6 is a perspective view of an assembly ring for the needle tube and gripping plate, FIG. 7 is a longitudinal section through an assembled needle, and FIG. 8 is a perspective view of another embodiment of a gripping plate portion.

With reference to the drawings it will be seen that in FIG. 1 the two sheet metal blanks (1) and (2) are illustrated from which the needle tube is formed. Each blank has an integral wing (3) provided with perforations (4). The blank (2) is also provided with a dot elevation (5) before its pointed end. This elevation may be obtained by grinding down the inner surface of the tube or by bonding an elevated point to the surface. The purpose of the elevation (5) is to keep the inserted catheter away from the sharp tube point during insertion thereof, and also when it is withdrawn. The upper tube portion (1) has an indented portion at its front edge which corresponds in projection approximately to a half-ellipse. This front edge is rounded or/and polished. The two semicircular metallic tube sections 1 and 2 are placed upon each other and bonded together along their longitudinal edges 6 so as to form a cylindrical needle tube, and the needle tube formed by these differently treated two portions thus presents at its front end an opening which is slanted in relation to its central axis and when seen in plan view corresponds to the slanted end of a conventional injection needle provided with the above mentioned small elevation in its forward area. At the rearward end of the tube both portions (1) and (2) each have a flat extension or wing (3) of the same material having one or more perforations (4). The two wings (2) extend horizontally away from the separation line of the tube. They are surrounded by a gripping plate of thermoplastic material which also consists of two symmetrical portions. These portions present at their inner surface the negative image of a metal wing and on one side slightly conical elevations (7) which correspond to the perforations (4) of wings (3). On the other side of this tube portion recesses (8) are provided which correspond to the conical elevation (7) of the symmetrical second gripping plate portion. The conical elevations (7) are of such a size that they can lodge into the perforations (4) of the metal wings (3) so that a secure connection between them is obtained. In assembling the metal and thermoplastic parts of the needle it is obtained that in each instance a metal tube portion with its wing (3) extending substantially at right angle is securely connected with a gripping plate portion while the gripping plate portions themselves are secured by their elevations (7) and recesses (8) only against a sliding movement, but may be separated from each other. The gripping plate portions have grooves (9) extending in the direction of the tube axis and surround the tube when the gripping plate is closed. On the side opposite the tube point the two gripping plate portions combine to form a cylinder which extends beyond them. This cylinder has a conical bore (11) along its central axis which leads into the tube. Each half of the cylinder is formed by a gripping plate portion. Both cylinder halves (10) have a flexible gripping tongue (12) at their outer edge which serves to separate the tube. The two half-cylinders 10 are also surrounded by a rigid band (13) which keeps the gripping plate portions assembled and which may be pulled off before the tube is separated.

The sealing of the needle tube is carried out according to the invention on the inside by a suitable sealing element (14). It consists of a plastic and/or elastic inner tube which engages the inside of the syringe tube in a sealing relationship and extends into close proximity of the insertion opening of the tube. The sealing by means of this inner tube can be obtained in various ways: for example a hose or tube of thermoplastic material may be used whose outer diameter is slightly less than the lumen of the syringe tube. After its insertion it is subjected to a brief heat treatment so that it shrinks and engages the inner wall of the tube in a sealing relationship. It is known that when tubes made of certain thermoplastic materials shrink axially under heat treatment they will simultaneously expand diametrically, and it is this diametric expansion that will cause such a thermoplastic tube to engage the needle tube's inner wall. It is also possible to use an inner tube of a semi-elastic material such as soft-PVC whose diameter is slightly larger than the lumen of the needle tube. For its insertion the inner tube is stretched in the longitudinal direction so that its diameter decreases and it can be introduced into the needle tube. As the material has the property to return slowly to its original shape the inner tube contracts gradually and engages the inner wall of the needle tube in a sealing manner. A further possibility to provide an air tight sealing of the needle tube is to introduce a longitudinally stretched elastic rubber inner tube which after releasing the tension increases in diameter and engages the inner wall of the needle tube in a sealing relationship. On the side (15) of the sealing element (14) opposite the needle tube point the sealing element is appropriately expanded to a cone. This cone is designed to receive on its inside the needle cone of an injection syringe. Its outer surface fits into the conical bore (11) of the cylinder which is formed by the two gripping plate portions. This cone extends outwardly far enough so that it can be gripped with two fingers and thereby the entire sealing element (14) can be removed from the needle tube together with the injection syringe used to insert the needle and can be replaced by an insertion device for the sterile vessel catheter.

Through this insertion device the catheter, which is protected by a thin walled foil tube, is inserted in a sensitive manner into the blood vessel of the patient. Thereafter, the needle tube is withdrawn from the body and is slid along the catheter. The catheter insertion device, as well as the rigid ring (13) which holds the two half-cylinders (10) of the gripping plate portions together, is then pulled off and withdrawn over the catheter end cone. Thereafter, the gripping plate can be pulled apart by the two flexible tongues (12) fixed to the cylindrical extensions of the gripping plates, whereby the gripping plate separates into two parts. Upon a further pull on the tongues (12), the bonding connection of the two metal tube parts (1) and (2) is pulled apart so that the catheter end of the needle tube is opened.

Referring now to the second embodiment of the invention as shown in FIG. 8, the two-part gripping plate of the needle tube has besides the central bore (9) which leads forward into the metal needle tube and rearward into the cone of the cylinder formed by the two parts (10) also at least one additional bore (11a) or (11b) in the contact surface of the two gripping plate portions which leads diagonally into the central bore (9) just before the rearward end of the metal tube portions forming the needle. This bore (11a) or (11b) expands conically toward the edge of the gripping plate in order to receive the insertion device of the catheter. Before removing the sealing element (14) together with the injection syringe a small tension is imparted to the catheter which may then be introduced by its insertion device into this laterally disposed cone so that it tends to push forward. As soon as the sealing element (14) frees the central bore (9) when it is withdrawn the catheter will penetrate into the central bore (9) and thus close the syringe tube so that no blood can escape. The above mentioned tensioning can also be obtained by pushing the catheter by means of a clamp in the plastic tube for keeping it sterile in the direction of the insertion device so that it bends into a wave shape and thus has an inner forward tension. It is appropriate to provide not only one but two lateral bores (11a) and (11b) for the catheter insertion devices at both sides of the central cylinder in the separation surface of the gripping plate so that the practicing doctor has the possibility, depending on the position of the patient or of the puncture area, to select the opening of the gripping plate for the insertion of the catheter that is the most easily accessible. The additional bores of the gripping plate described can be closed with sealing plugs which are removed when necessary.

What is claimed is:

1. A separable catheter needle assembly for use in inserting a flexible vessel catheter into a blood vessel, comprising:
   a pair of semicylindrical needle tube portions made of metal, and bonded together along their longitudinal edges in face-to-face relationship to form a needle tube;
   one of said semicylindrical needle tube portions having a sharp point on the front end thereof; and
   a tubular sealing element disposed within said needle tube and extending for substantially the full length thereof, said tubular sealing element engaging the inner wall of said needle tube and sealing the interior thereof against leakage through said bonded longitudinal edges, and including a rear portion that projects outwardly a substantial distance from the rear end of said needle tube, to provide means for gripping said element for removing it from said needle tube.

2. A catheter needle assembly as recited in claim 1, including additionally:
   a rounded elevation on the interior surface of said semicylindrical needle tube portion carrying said sharp point, said elevation being positioned adjacent said sharp point and serving to prevent a catheter being passed through said needle tube from being damaged by said sharp point.

3. A catheter needle assembly as recited in claim 1, wherein said tubular sealing element is made of thermoplastic material.

4. A catheter needle assembly as recited in claim 1, wherein said tubular sealing element is made of an elastic rubber material.

5. A catheter needle assembly as recited in claim 1, wherein said tubular sealing element has an outer diameter slightly larger than the inner diameter of said needle tube, and is made of a semielastic material.

6. A separable catheter needle assembly for use in inserting a flexible vessel catheter into a blood vessel, comprising:
   a pair of semicylindrical needle tube portions made of metal, each of said portions having a laterally extending wing on the rear end thereof, the forward end of one of said tube portions being sharply pointed, and said tube portions being bonded together along their longitudinal edges in face-to-face relationship to form a needle tube;
   the wings on said tube portions projecting oppositely and lying in a common plane when said tube portions are in assembled relationship to form said needle tube;
   a pair of gripping plates adapted and arranged to fit about said rear end of said tube portions and said wings in engaged relationship, said gripping plates when in engaged, assembled relationship forming a central bore within which the rear portion of said needle tube is received;
   means for holding said gripping plates in assembled relationship; and
   a tubular sealing element disposed within said needle tube and extending for substantially the full length thereof, said tubular sealing element engaging the inner wall of said needle tube and sealing the interior thereof against leakage through said bonded longitudinal edges, and including a rear portion that projects outwardly a substantial distance from the rear end of said needle tube and from said pair of assembled gripping plates, to provide means for gripping said element for removing it from said needle tube.

7. A catheter needle assembly as recited in claim 6, wherein each of said wings has at least one perforation therethrough, and wherein said gripping plates carry projection means arranged to engage within said perforations to secure said gripping plates to said wings, one wing to each gripping plate.

8. A catheter needle assembly as recited in claim 7, wherein each of said gripping plates includes an extension on the rear end thereof, said extensions mating when said plates are in assembled relationship and containing a bore from which said projecting rear portion of said tubular sealing element projects, said means for holding said gripping plates in assembled relationship comprising a ring element receivable on said mated extensions.

9. A catheter needle assembly as recited in claim 8, wherein said gripping plates carry flexible gripping tongues on said extensions, for use in separating said gripping plates after removal of said ring element.

10. A catheter needle assembly as recited in claim 8, wherein said projecting rear portion of said tubular sealing element has a frusto-conical bore in the outer end thereof and has an enlarged diameter relative to the remainder of said sealing element, said bore formed by said extensions being shaped to seat said enlarged projecting rear portion of said tubular sealing element.

11. A catheter needle assembly as recited in claim 8, wherein in addition to said central bore formed thereby, said pair of gripping plates also form therebetween at least one additional bore that intersects said central bore at an angle, for receiving a separable catheter insertion device.

* * * * *